United States Patent
Lee et al.

(10) Patent No.: US 9,744,257 B2
(45) Date of Patent: Aug. 29, 2017

(54) LED PHOTOCATALYST MODULE USING PHOTOCATALYST

(71) Applicant: LG Hausys, Ltd., Seoul (KR)

(72) Inventors: Dong-Il Lee, Anyang-si (KR);
Joo-Hwan Seo, Seoul (KR);
Seong-Moon Jung, Daejeon (KR)

(73) Assignee: LG HAUSYS, LTD., Seoul (KR)

( * ) Notice: Subject to any disclaimer, the term of this patent is extended or adjusted under 35 U.S.C. 154(b) by 0 days.

(21) Appl. No.: 15/022,560

(22) PCT Filed: Sep. 4, 2014

(86) PCT No.: PCT/KR2014/008300
§ 371 (c)(1),
(2) Date: Mar. 16, 2016

(87) PCT Pub. No.: WO2015/046777
PCT Pub. Date: Apr. 2, 2015

(65) Prior Publication Data
US 2016/0220721 A1 Aug. 4, 2016

(30) Foreign Application Priority Data
Sep. 26, 2013 (KR) .................. 10-2013-0114222

(51) Int. Cl.
*A61L 9/00* (2006.01)
*A61L 9/20* (2006.01)
(Continued)

(52) U.S. Cl.
CPC ............. *A61L 9/205* (2013.01); *B01J 21/063* (2013.01); *B01J 23/02* (2013.01); *B01J 23/06* (2013.01);
(Continued)

(58) Field of Classification Search
CPC .................................. A61L 9/205; F24F 6/12
(Continued)

(56) References Cited

U.S. PATENT DOCUMENTS

6,326,079 B1 12/2001 Philippe et al.
2013/0330238 A1* 12/2013 Lee .................... B01D 53/0407
422/123

FOREIGN PATENT DOCUMENTS

KR 1020060092169 A 8/2006
KR 100808343 B1 2/2008
(Continued)

OTHER PUBLICATIONS

International Search Report mailed Dec. 17, 2014 corresponding to International Application No. PCT/KR2014/008300.

*Primary Examiner* — Monzer R Chorbaji
(74) *Attorney, Agent, or Firm* — Hauptman Ham, LLP

(57) ABSTRACT

The present invention relates to an LED photocatalyst module comprising: a light supplying unit for irradiating light onto a photocatalyst so that the photocatalyst is activated; a photocatalyst purifying unit disposed spaced apart from the light supplying unit and purifying polluted air; and a discharging unit disposed spaced apart from the photocatalyst purifying unit and sucking in the air purified by the photocatalyst purifying unit and discharging the air to the outside, wherein the photocatalyst purifying unit includes a ceramic honeycomb structure in which a plurality of photocatalyst pores, coated with the photocatalyst, are combined in a honeycomb pattern, and the photocatalyst includes a porous metal oxide film and metal particles formed on a surface of the porous metal oxide film.

13 Claims, 1 Drawing Sheet

(51) Int. Cl.

| | | |
|---|---|---|
| *B01J 21/06* | (2006.01) | |
| *B01J 23/02* | (2006.01) | |
| *B01J 23/06* | (2006.01) | |
| *B01J 23/10* | (2006.01) | |
| *B01J 23/22* | (2006.01) | |
| *B01J 23/26* | (2006.01) | |
| *B01J 23/28* | (2006.01) | |
| *B01J 23/30* | (2006.01) | |
| *B01J 23/34* | (2006.01) | |
| *B01J 23/42* | (2006.01) | |
| *B01J 23/50* | (2006.01) | |
| *B01J 23/52* | (2006.01) | |
| *B01J 23/72* | (2006.01) | |
| *B01J 23/745* | (2006.01) | |
| *B01J 23/75* | (2006.01) | |
| *B01J 23/755* | (2006.01) | |

(52) U.S. Cl.
   CPC .............. *B01J 23/10* (2013.01); *B01J 23/22* (2013.01); *B01J 23/26* (2013.01); *B01J 23/28* (2013.01); *B01J 23/30* (2013.01); *B01J 23/34* (2013.01); *B01J 23/42* (2013.01); *B01J 23/50* (2013.01); *B01J 23/52* (2013.01); *B01J 23/72* (2013.01); *B01J 23/745* (2013.01); *B01J 23/75* (2013.01); *B01J 23/755* (2013.01)

(58) Field of Classification Search
   USPC ........................................ 422/120, 123, 306
   See application file for complete search history.

(56) References Cited

FOREIGN PATENT DOCUMENTS

| KR | 100834585 B1 | 6/2008 |
|---|---|---|
| KR | 101267628 B1 | 5/2013 |

\* cited by examiner

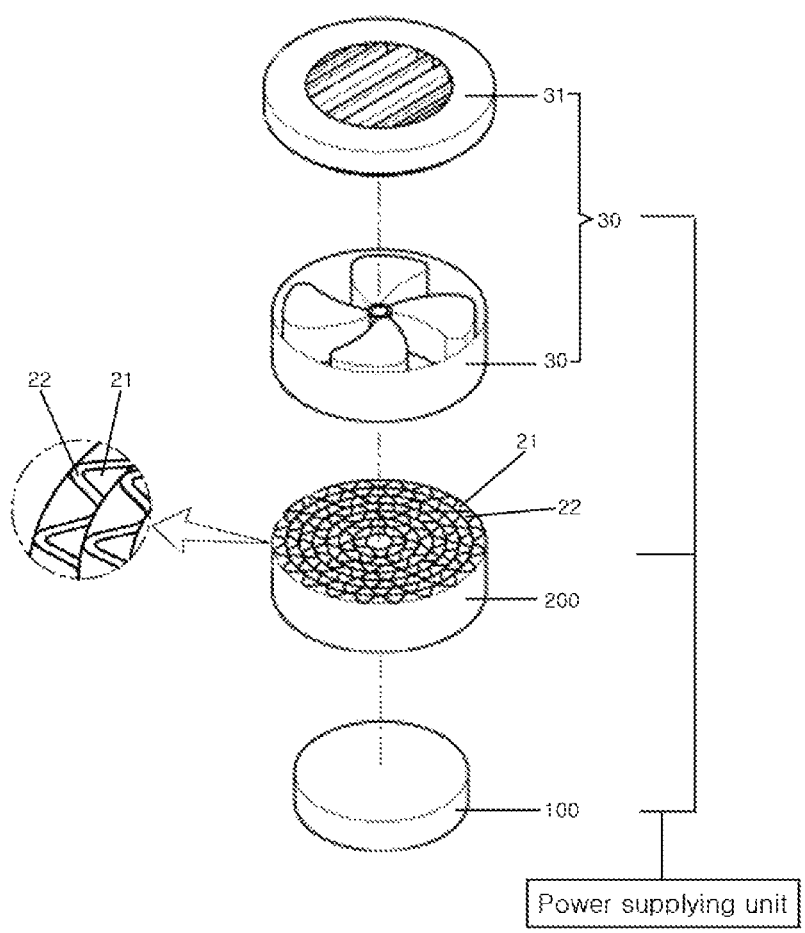

LED PHOTOCATALYST MODULE USING PHOTOCATALYST

TECHNICAL FIELD

The present invention relates to a light-emitting diode (LED) photocatalyst module using a photocatalyst.

BACKGROUND ART

As air pollution becomes severe and people stay indoors longer in modern society, the demand for improving indoor air quality has been increased. In addition, as risks of diseases by emergence of infectious viruses are recently increased, and toxicity of a humidifier disinfectant was a social issue years ago, antimicrobial and bactericidal products that are harmless to human being are required.

In this respect, air purification technology using a photocatalyst has received a lot of attention, and various forms of products are commercially available.

However, in the case of universal products such as one using a powder or a coating liquid, performance differs portion to portion depending on the amount of such a powder or coating liquid applied. On the other hand, products such as an air cleaner provided with a photocatalyst and a light source are not possible to be variously applied as a single product.

Accordingly, users still demand a small LED photocatalyst module that utilizes a photocatalyst having high activity even in the visible light LED, removes hazardous materials, and has excellent deodorizing and antibacterial functions.

DISCLOSURE

Technical Problem

It is an aspect of the present invention to provide an LED photocatalyst module including a photocatalyst having excellent photocatalytic efficiency in response to visible light.

Technical Solution

In accordance with one aspect of the present invention, a light-emitting diode (LED) photocatalyst module includes: a light supplying unit for irradiating light onto a photocatalyst so that the photocatalyst is activated; a photocatalyst purifying unit being disposed spaced apart from the light supplying unit and purifying polluted air; and a discharging unit being disposed spaced apart from the photocatalyst purifying unit and sucking in the air purified by the photocatalyst purifying unit and discharging the air to the outside, wherein the photocatalyst purifying unit includes a ceramic honeycomb structure in which a plurality of photocatalyst pores, coated with the photocatalyst, are combined in a honeycomb pattern, and the photocatalyst includes a porous metal oxide film and metal particles formed on a surface of the porous metal oxide film.

The metal oxide film may include at least one metal oxide selected from the group consisting of titanium oxide, tungsten oxide, zinc oxide, niobium oxide, and combinations thereof.

The metal may include at least one selected from the group consisting of tungsten, chromium, vanadium, molybdenum, copper, iron, cobalt, manganese, nickel, platinum, gold, silver, cerium, cadmium, zinc, magnesium, calcium, strontium, barium, and combinations thereof.

The porous metal oxide film may have a porosity of about 5% to about 50%.

The porous metal oxide film may have a specific surface area of about 50 $m^2/g$ to about 500 $m^2/g$.

The metal particles may have a content of about 0.0001 mg to about 0.01 mg per 1 $cm^2$ of a plane of the porous metal oxide film.

The metal particles may have a content of about 0.01 wt % to about 10 wt % relative to 100 wt % of the photocatalyst.

The ceramic honeycomb structure may have a porosity of about 50% to about 80%.

The light supplying unit may include an emitter formed of a light-emitting diode (LED), and the discharging unit may include: a discharging plate through which a plurality of through holes are formed; and a discharging fan formed in the bottom of the discharging plate, which sucks in the purified air and discharges the air through the discharging plate.

The LED photocatalyst module may include: a power supplying unit for supplying power so as to control the light supplying unit, the photocatalyst purifying unit, and the discharging unit.

The LED photocatalyst module may have a hazardous gas removal rate of about 80% to about 90%.

The hazardous gas may be at least one selected from the group consisting of volatile organic compounds (VOCs), perfluorocarbons (PFCs), Chlorofluorocarbons (CFCs), trichloroethylene (TCE), dioxin, and nitrogen oxide.

Advantageous Effects

The light-emitting diode (LED) photocatalyst module according to the present invention may remove hazardous materials, and have excellent deodorizing and antibacterial effects.

In addition, the LED photocatalyst module according to the present invention may be applied to various application fields related with removal of the hazardous materials, and may secure reliability to photocatalyst performance.

DESCRIPTION OF DRAWINGS

FIG. 1 is an exploded view of a light-emitting diode (LED) photocatalyst module according to an exemplary embodiment of the present invention.

BEST MODE

Hereinafter, exemplary embodiments of the present invention will be described in detail. However, these exemplary embodiments are only provided by way of example, and the present invention is not limited to these exemplary embodiments. Therefore, the present invention will be defined only by the scope of the appended claims.

In an exemplary embodiment of the present invention, there is provided a light-emitting diode (LED) photocatalyst module including: a light supplying unit for irradiating light onto a photocatalyst so that the photocatalyst is activated; a photocatalyst purifying unit disposed spaced apart from the light supplying unit and purifying polluted air; and a discharging unit disposed spaced apart from the photocatalyst purifying unit and sucking in the air purified by the photocatalyst purifying unit and discharging the air to the outside, wherein the photocatalyst purifying unit includes a ceramic honeycomb structure in which a plurality of photocatalyst pores, coated with the photocatalyst, are combined in a honeycomb pattern, and the photocatalyst includes a porous metal oxide film and metal particles formed on a surface of the porous metal oxide film.

In general air conditional products using a $TiO_2$ photocatalyst, there are a lot of limitations according to system design for minimizing ultraviolet radiation (UV) exposure due to limitations in which UV is required to be used as a light source, and there are problems such as ozone occurrence due to UV, etc. Further, products using a photocatalyst response to fluorescent light have a limitation in being minimized due to application of the fluorescent light, such that there is a difficulty in being variously applied.

In contrast, the LED photocatalyst module may remove hazardous materials, and have deodorizing and antibacterial functions by using a visible photocatalyst having a high activity even under a light-emitting diode (LED).

Specifically, a ceramic honeycomb structure including the photocatalyst purifying unit may be coated with the photocatalyst including the porous metal oxide film and the metal particles formed on the surface of the porous metal oxide film. For example, the ceramic honeycomb structure may be coated with the photocatalyst ($Pt/WO_3$) including $WO_3$ and Pt formed on the surface of $WO_3$. The ceramic honeycomb structure coated with the photocatalyst may secure an excellent performance of removing hazardous materials under the visible LED.

A method of coating the ceramic honeycomb structure with the photocatalyst may include a process of coating the ceramic honeycomb structure with the porous metal oxide film, and doping metal particles thereon by photo-deposition.

Metal oxides forming the porous metal oxide film may be used without limitation as long as it is known in the art as a metal oxide used as the photocatalyst. Metals of the metal particles may be any kind of metal as long as it is doped on the metal oxide to be capable of providing activity for visible light. The metals of the metal particles may be, for example, a transition metal, a precious metal, etc.

The photocatalyst is a material agent in which electrons and holes produced from energy obtained by absorbing light generate superoxide anions or hydroxyl radicals, thereby having air cleaning, deodorant, and antibacterial functions. For example, the superoxide anions or hydroxyl radicals produced from the photocatalyst may decompose hazardous environment materials such as formaldehyde. Moreover, since the photocatalyst may have an absorption rate with respect to the visible light to have an excellent efficiency even for indoor light source, separate ultraviolet suppliers may not be required.

The metal oxide film may include at least one metal oxide selected from the group consisting of titanium oxide, tungsten oxide, zinc oxide, niobium oxide, and combinations thereof.

In addition, the metal may include at least one selected from the group consisting of tungsten, chromium, vanadium, molybdenum, copper, iron, cobalt, manganese, nickel, platinum, gold, silver, cerium, cadmium, zinc, magnesium, calcium, strontium, barium, and combinations thereof.

For example, the photocatalyst ($TiO_2$—Pt) including titanium oxide and platinum particles formed on the surface of titanium oxide and the photocatalyst ($WO_3$—Pt) including tungsten oxide and platinum particles formed on the surface of tungsten oxide, may be used.

Specifically, $TiO_2$—Pt is responsive only to the ultraviolet, and is required to use an ultraviolet-LED even in the case of using LED, such that $TiO_2$—Pt may have a problem in view of cost, and may have a difficulty in being applied to the visible light LED photocatalyst module. However, the $WO_3$—Pt photocatalyst provides the photocatalyst performance by doping platinum (Pt), and the amount of Pt used in the $WO_3$—Pt photocatalyst is less than that of the $TiO_2$—Pt photocatalyst, such that the $WO_3$—Pt photocatalyst may have a benefit in view of cost, and may have an advantage of being applied to the visible light LED photocatalyst module.

The porous metal oxide film may have a porosity of about 5% to about 50%. Within the above-described range of porosity, the photocatalyst may have more excellent activity efficiency for visible light. When the porous metal oxide film does not have a porosity but is densely formed by a sputtering method, etc., absorption of reaction materials such as formaldehyde, etc., is not effectively performed, such that it is difficult to expect an excellent photocatalyst activity.

The porous metal oxide film may have a specific surface area of about 50 $m^2/g$ to about 500 $m^2/g$. Within the above-described range of specific surface area, the photocatalyst may have more excellent activity efficiency for visible light.

In addition, the metal particles may have a content of about 0.01 wt % to about 10 wt % relative to 100 wt % of the photocatalyst. The metal particles are doped on the surface of the porous metal oxide film by photo-deposition, and may provide photocatalyst performance by controlling the content thereof. Here, when the content of the photocatalyst is maintained within the above-described range, the photocatalyst effect under visible light may be easily implemented.

Specifically, in the $TiO_2$—Pt photocatalyst, platinum (Pt) may have a content of about 0.1 wt % to about 10 wt % relative to 100 wt % of the photocatalyst, and in the $WO_3$—Pt photocatalyst, platinum (Pt) may have a content of about 0.01 wt % to about 1 wt % relative to 100 wt % of the photocatalyst.

More specifically, since the $TiO_2$—Pt photocatalyst has a low visible light absorption rate, a relatively large content of platinum (Pt) is required as compared to the $WO_3$—Pt photocatalyst so as to improve the visible light absorption rate by the addition of platinum (Pt). In the $WO_3$—Pt photocatalyst, when the platinum (Pt) is added in a content less than 0.01 wt %, an electron-hole recombination-inhibition effect by the addition of platinum (Pt) is reduced, which may deteriorate the activity, and when the platinum (Pt) is added in a content more than 1 wt %, a photocatalyst activity point is reduced, which may deteriorate reactivity.

FIG. 1 is an exploded view of a lighting-emitting diode (LED) photocatalyst module according to an exemplary embodiment of the present invention. Referring to FIG. 1, the LED photocatalyst module may include the light supplying unit 100, the photocatalyst purifying unit 200, and the discharging unit 300, and the photocatalyst purifying unit may include the ceramic honeycomb structure in which the plurality of photocatalyst pores 21, coated with the photocatalyst 22, are combined in a honeycomb pattern.

The reason in which the plurality of photocatalyst pores 21 are formed in the ceramic honeycomb structure is to provide a large amount of photocatalyst 22 in a confined space in the photocatalyst pores 21.

The ceramic honeycomb structure may have a porosity of about 50% to about 80%. The ceramic honeycomb structure may include the plurality of photocatalyst pores 21 to have a predetermined porosity, and may increase a support amount of the photocatalyst by having the above-described range porosity. When the porosity of the ceramic honeycomb structure is less than about 50%, since the support amount of the photocatalyst is not sufficient, it is difficult to have desired activity, and when the porosity of the ceramic honeycomb structure is more than about 80%, since structural strength is weaken, formability may be limited.

The light supplying unit may include an emitter formed of a light-emitting diode (LED). The light supplying unit 100 irradiates light onto the photocatalyst 22 coated on the ceramic honeycomb structure so that the photocatalyst is activated.

The light supplying unit 100 includes an emitter formed of a light-emitting diode (LED). As described above, in the emitter formed of the light-emitting diode (LED), the LED is an example, but various lamps (not shown) may also be used in accordance with the user's need. In particular, the emitter may irradiate visible light through a separate lamp capable of irradiating visible light. As a result, the emitter is possible to irradiate a visible light region, and the photocatalyst 22 refers to a material accepting light to promote a chemical reaction, wherein the reaction is referred to as a photochemical reaction.

Further, the light supplying unit 100 is provided with a visible light source rather than an ultraviolet light source, such that illumination required for the photocatalyst may be secured to provide reliable performance, and the ceramic honeycomb structure having a high surface area may be used to secure a predetermined performance even in a small size and may be formed in a module form, thereby being easily applied to various application fields without adding separate facilities.

The discharging unit 300 is disposed to the top of the photocatalyst purifying unit 200. In addition, the discharging unit 300 may include: a discharging plate 31 through which a plurality of through holes are formed; and a discharging fan 30 formed in the bottom of the discharging plate, which sucks in the purified air and discharges the air through the discharging plate.

The discharging unit 300 may include: the discharging plate 31 through which the plurality of through holes are formed. Only the air purified while passing through the photocatalyst purifying unit 200 may be discharged to the outside through the through holes of the discharging plate 31. Here, the discharging fan 30 functions to allow the purified air to be more smoothly discharged through the discharging plate 31.

The LED photocatalyst module may include a power supplying unit for supplying power so as to control the light supplying unit 100, the photocatalyst purifying unit 200, and the discharging unit 300. The power supplying unit may control the light supplying unit 100, the photocatalyst purifying unit 200, and the discharging unit 300 through a mechanism for supplying power. Each configuration is controlled and organically operated, thereby providing an LED photocatalyst module having more excellent photocatalytic function.

The LED photocatalyst module may have a hazardous gas removal rate of about 80% to about 90%. Specifically, the hazardous gas removal rate is calculated by measuring a concentration of a hazardous gas before entering a chamber installed with the LED photocatalyst module, and a concentration of the hazardous gas after being passed through the chamber. For the concentration, the hazardous gas was concentrated to be an amount for 10 L using DNPH (2,4-dinitrophenylhydrazine) cartridge, and analyzed by HPLC (Agilent Technologies, Inc).

More specifically, the hazardous gas may be at least one selected from the group consisting of formaldehyde, volatile organic compounds (VOCs), perfluorocarbons (PFCs), Chlorofluorocarbons (CFCs), trichloroethylene (TCE), dioxin, and nitrogen oxide.

The lighting-emitting diode (LED) photocatalyst module may remove hazardous materials, and have excellent deodorizing and antibacterial effects. In addition, the LED photocatalyst module according to the present invention may be applied to various application fields related with removal of the hazardous materials, and may secure reliability to photocatalyst performance.

Hereinafter, specific Examples of the present invention will be provided. It is to be noted that Examples to be described below are provided merely for specifically exemplifying or explaining the present invention, and accordingly, the present invention is not limited to the following Examples.

EXAMPLES

Example 1

Nano powder (Aldrich chemical company) was used for tungsten trioxide ($WO_3$). The $WO_3$ was dispersed in isopropanol to prepare a $WO_3$ isopropanol slurry having a concentration of 10 wt %. The slurry was treated by a homogenizer for 30 minutes to obtain a uniform dispersion, and the uniform dispersion was dip-coated on a ceramic honeycomb structure by using $TiO_2$ sol as a binder. The ceramic honeycomb structure coated with $WO_3$ was subjected to photo-deposition to thereby dope platinum (Pt) thereon, and the ceramic honeycomb structure coated with $WO_3$ was soaked in 0.0001 wt % of $H_2PtCl_6$ aqueous solution. Then, photo-deposition was performed with Pt under UV lamp, thereby manufacturing the ceramic honeycomb structure coated with Pt/$WO_3$ photocatalyst. The metal oxide film ($WO_3$) of the manufactured Pt/$WO_3$ photocatalyst had a porosity of about 20% and a specific surface area of about 56 $m^2$/g, and had a content of 0.1 wt % relative to 100 wt % of the photocatalyst of the metal particles (Pt).

Example 2

A ceramic honeycomb structure coated with a Pt/$WO_3$ photocatalyst was manufactured by the same method as Example 1 except for changing the concentration of the $H_2PtCl_6$ aqueous solution to 0.0005 wt %. The metal oxide film ($WO_3$) of the manufactured Pt/$WO_3$ photocatalyst had a porosity of about 20% and a specific surface area of about 55 $m^2$/g, and had a content of 0.5 wt % relative to 100 wt % of the photocatalyst of the metal particles (Pt).

Example 3

A ceramic honeycomb structure coated with a Pt/$TiO_2$ photocatalyst was manufactured by the same method as Example 2 except for using $TiO_2$ (P25, Degussa) instead of using $WO_3$. The metal oxide film ($TiO_2$) of the manufactured Pt/$TiO_2$ photocatalyst had a porosity of about 30% and a specific surface area of about 60 $m^2$/g, and had a content of 0.5 wt % relative to 100 wt % of the photocatalyst of the metal particles (Pt).

Experimental Example

Performance for removing formaldehyde was evaluated on the photocatalysts of Examples and Comparative Example. Each ceramic honeycomb structure (80 mm diameter×15 mm height) coated with the photocatalyst manufactured by Examples and Comparative Example was installed in 20 L small chamber (ADTEC Inc.), and clean air having a formaldehyde concentration of 0.08 ppm was allowed to continuously flow at a flow rate of 167 cc/min so that the number of ventilations was adjusted to be 0.5 times/hr. The LED 20 W module was used as a light source. Each formaldehyde removal rate was calculated by measuring a concentration of formaldehyde before entering the chamber, and a concentration of formaldehyde after being passed through the chamber, and the calculated values were shown in Table 1 below. For the concentration, formaldehyde was concentrated to be an amount for 10 L using DNPH (2,4-dinitrophenylhydrazine) cartridge, and analyzed by HPLC (Agilent Technologies, Inc.).

TABLE 1

| Classification | Formaldehyde Removal Rate (%) |
| --- | --- |
| Example 1 | 90% |
| Example 2 | 90% |
| Example 3 | 57% |

In Examples 1 to 3, the photocatalysts including the porous metal oxide film and the metal particles formed on the surface of the porous metal oxide film, were used. It was confirmed that formaldehyde was removed from the photocatalysts of Examples 1 to 3.

Specifically, the $Pt/WO_3$ photocatalyst was used in Examples 1 and 2, and the $Pt/TiO_2$ photocatalyst was used in Example 3, such that it could be appreciated that the photocatalysts of Examples 1 and 2 had excellent formaldehyde removal rate as compared to the photocatalyst of Example 3.

The invention claimed is:

1. A light-emitting diode (LED) photocatalyst module comprising:
   a light supplying unit for irradiating light onto a photocatalyst so that the photocatalyst is activated;
   a photocatalyst purifying unit being disposed spaced apart from the light supplying unit and purifying polluted air; and
   a discharging unit being disposed spaced apart from the photocatalyst purifying unit and sucking in the air purified by the photocatalyst purifying unit and discharging the air to the outside,
   wherein the photocatalyst purifying unit includes a ceramic honeycomb structure in which a plurality of photocatalyst pores, coated with the photocatalyst, are combined in a honeycomb pattern,
   wherein the photocatalyst includes a porous metal oxide film and metal particles formed on a surface of the porous metal oxide film, and
   wherein the porous metal oxide film comprises tungsten oxide.

2. The LED photocatalyst module of claim 1, wherein the metal oxide film further includes at least one metal oxide selected from the group consisting of titanium oxide, zinc oxide, niobium oxide, and combinations thereof.

3. The LED photocatalyst module of claim 1, wherein the metal particle includes at least one selected from the group consisting of tungsten, chromium, vanadium, molybdenum, copper, iron, cobalt, manganese, nickel, platinum, gold, silver, cerium, cadmium, zinc, magnesium, calcium, strontium, barium, and combinations thereof.

4. The LED photocatalyst module of claim 1, wherein the porous metal oxide film has a porosity of 5% to 50%.

5. The LED photocatalyst module of claim 1, wherein the porous metal oxide film has a specific surface area of 50 $m^2/g$ to 500 $m^2/g$.

6. The LED photocatalyst module of claim 1, wherein the metal particles have a content of 0.0001 mg to 0.01 mg per 1 $cm^2$ of a plane of the porous metal oxide film.

7. The LED photocatalyst module of claim 1, wherein the metal particles have a content of 0.01 wt % to 10 wt % relative to 100 wt % of the photocatalyst.

8. The LED photocatalyst module of claim 1, wherein the ceramic honeycomb structure has a porosity of 50% to 80%.

9. The LED photocatalyst module of claim 1, wherein the light supplying unit includes an emitter formed of a light-emitting diode (LED).

10. The LED photocatalyst module of claim 1, wherein the discharging unit includes:
    a discharging plate through which a plurality of through holes are formed; and
    a discharging fan formed in the bottom of the discharging plate, which sucks in the purified air and discharges the air through the discharging plate.

11. The LED photocatalyst module of claim 1, comprising: a power supplying unit for supplying power so as to control the light supplying unit, the photocatalyst purifying unit, and the discharging unit.

12. The LED photocatalyst module of claim 1, wherein the LED photocatalyst module has a hazardous gas removal rate of 80% to 90%.

13. The LED photocatalyst module of claim 12, wherein the hazardous gas is at least one selected from the group consisting of volatile organic compounds (VOCs), perfluorocarbons (PFCs), chlorofluorocarbons (CFCs), trichloroethylene (TCE), dioxin, and nitrogen oxide.

* * * * *